United States Patent [19]

McFarland

[11] Patent Number: 4,658,080

[45] Date of Patent: * Apr. 14, 1987

[54] ACETYLENE REMOVAL PROCESS

[75] Inventor: Cecil G. McFarland, Houston, Tex.

[73] Assignee: Petro-Tex Chemical Corporation, Houston, Tex.

[*] Notice: The portion of the term of this patent subsequent to Apr. 23, 2002 has been disclaimed.

[21] Appl. No.: 523,291

[22] Filed: Aug. 15, 1983

Related U.S. Application Data

[60] Continuation of Ser. No. 088,394, Oct. 26, 1979, abandoned, which is a continuation-in-part of Ser. No. 566,303, Apr. 9, 1975, abandoned, which is a division of Ser. No. 443,752, Feb. 19, 1974, abandoned.

[51] Int. Cl.$^4$ ............................................. C07C 5/327
[52] U.S. Cl. .................................... 585/658; 585/661; 585/260; 585/262
[58] Field of Search ................. 585/260, 262, 658, 661

[56] References Cited

U.S. PATENT DOCUMENTS

| | | | |
|---|---|---|---|
| 1,910,837 | 5/1933 | Jaeger | 260/677 A |
| 2,511,453 | 6/1950 | Barry | 260/677 H |
| 3,274,286 | 9/1966 | Reich | 260/681.5 R |
| 3,444,256 | 5/1969 | Engelhard et al. | 260/681.5 R |
| 3,476,824 | 11/1969 | Woskow | 585/658 |
| 3,684,447 | 8/1972 | Johnston et al. | 423/658 |
| 3,686,347 | 8/1972 | Dean et al. | 260/680 E |
| 3,702,872 | 11/1972 | Manning et al. | 260/680 E |
| 3,725,493 | 4/1973 | Stine | 585/658 |

*Primary Examiner*—Natalie Trousof
*Assistant Examiner*—Joseph A. Boska
*Attorney, Agent, or Firm*—Kenneth H. Johnson

[57] ABSTRACT

A catalyst for removing acetylenic impurities from gaseous organic product streams, comprising at least Fe and Ni, other elements from Groups 8, 1b, 2b, 4b, 6b and 7b of the Periodic Table, an alkaline earth metal and an alkali metal.

5 Claims, No Drawings

ACETYLENE REMOVAL PROCESS

This application is a continuation of application Ser. No. 088,394, filed Oct. 26, 1979, now abandoned; which was a continuation-in-part of Ser. No. 566,303 filed Apr. 9, 1975, now abandoned, which was a division of Ser. No. 443,752 filed Feb. 19, 1974, now abandoned.

BACKGROUND OF THE INVENTION

The present invention relates to the process and catalyst for use therein for the selective removal of acetylenic compounds from gaseous streams. The process and catalyst of this invention are particularly useful for the reduction of acetylenic compound impurities from gaseous streams of organic compounds.

Terms "acetylenes" or "acetylenic compounds" are used to denote acetylene, vinyl acetylene, methyl acetylene, ethyl acetylene and the like. Such compounds are often found as impurities in various organic product streams. For example, the oxidative or non-oxidative dehydrogenation of $C_4$-$C_8$ hydrocarbons having at least one

grouping to produce the corresponding ethylenically unsaturated hydrocarbons produces small amounts of acetylenes. In many utilizations of the ethylenically unsaturated hydrocarbons, e.g., (butadiene) in the production of styrene-butadiene rubber, only small amounts, generally less than 1000 ppm acetylenes are acceptable in the butadiene. Similarly, in the production of olefinic hydrocarbons by the cracking of hydrocarbon feed streams, certain quantities of acetylenes are produced. Some ethylene recovery processes, for example, the cuprous salt method, necessitate that the acetylenes be first removed, since acetylene reacts with the cuprous ions to form an explosive compound. Furthermore, ethylene utilized for the purpose of polymerization requires an almost total removal of acetylenes.

Thus, a great effort has been expended to develop methods for removing acetylenes from organic streams, particularly $C_2$-$C_8$ paraffinic and olefinic hydrocarbons. Two approaches have been employed (1) physical, involving distillations, extractions, extractive distillation and various combinations of physical processes and (2) catalytic. Two catalytic approaches are shown in U.S. Pat. Nos. 3,476,824 and 3,728,412.

SUMMARY OF THE INVENTION

The present invention is the discovery of a catalyst and process for reducing the acetylenic compounds in a gaseous stream. In this invention the acetylenes are considered impurities. The gaseous stream would contain other organic compounds, particularly hydrocarbons which would be the principal or desired products of the stream. Preferred hydrocarbons would have 2 to 8 carbon atoms and more preferably 4 to 6 or 8 carbon atoms.

Briefly, the process comprises contacting a stream of organic compounds containing a minor amount of acetylenic compounds with a catalyst for reducing the amount of said acetylenic compounds in said stream, said catalyst comprising as the major cation elements by weight a member containing at least Fe and Ni, and selected from the group consisting of the elements of Periodic Table* Groups 8, 1b, 2b, 4b, 6b and 7b, an alkaline earth metal of Periodic Table Group 2a and an alkali metal of Periodic Table Group 1a.

*All references in this application are to the Periodic Table as found on page B-3 of the 51st. edition of the Handbook of Chemistry and Physics (1970-71) Chemical Rubber Publishing Company).

The present process and catalyst are particularly useful in a vapor phase oxidative dehydrogenation for the preparation of unsaturated hydrocarbons comprising oxidative dehydrogenation of a stream of hydrocarbon compounds to produce a product stream comprising unsaturated hydrocarbon product and as an impurity acetylenic compounds wherein the improvement comprises contacting the product stream in vapor phase at a temperature of at least 250° C. and containing less than 5 mol percent free oxygen with the solid catalyst as described above. A particular advantage of this invention is that the gaseous product stream is treated without the necessity for conversion to a liquid stream as is commonly done in prior acetylene separations.

DETAILED DESCRIPTION OF THE INVENTION

The acetylenic compounds are a serious contaminate in the unsaturated hydrocarbon product and must be essentially completely removed in order to have a product of suitable purity, i.e., a product having on the order of a few parts per million acetylenic compounds. The essentially complete removal of the acetylenic compound is quite difficult for several reasons. Principally, they constitute only a very minor percentage of the gaseous stream to be purified. Normally, acetylenic compounds will constitute less than 1.0 mol percent of the gaseous stream and usually may constitute less than or up to 0.5 mol percent of the gaseous stream. Generally the gaseous stream will contain at least about 3000 ppm acetylenic compounds based on the other organic compounds present such as the ethylenically unsaturated hydrocarbons. Their low concentration in the stream makes acetylenes quite difficult to remove. Moreover, azeotropes may form between the acetylenic compounds and the various other hydrocarbons present. Their low concentration in the stream and the closeness of the boiling points of acetylenes and other products make acetylenes quite difficult to remove. Moreover, azeotropes may form between the acetylenic compounds and the various other hydrocarbons present.

The organic compounds which can be treated according to the present invention generally have 2 to 20 carbon atoms. A preferred group of compounds are hydrocarbons and those having 2 to 8 carbon atoms or 4 to 6 carbon atoms. The process is a purification and hence the acetylenic compounds are present in only minor amounts in comparison to the other organic compounds in the stream. The major portion of the stream can be saturated and unsaturated (excluding acetylenic unsaturates) compounds and may comprise straight chain or branched compounds, similarly the desired compounds may be cyclic, acrylic or aromatic or mixtures of the foregoing. The acetylenic compounds will be preferentially reduced in the stream.

In general, the atoms of Fe, Ni, the other metals of Periodic Table Groups 8, 1b, 2b, 4b, 6b and 7b, the alkaline earth metals of Periodic Table Groups 2a and the alkali metals of Periodic Table Group 1a are effective in the process of this invention. The atoms may be present in the form of the metal compounds such as oxides, salts or hydroxides. Many of these metals, oxides, salts and hydroxides may change during the preparation of the catalyst, during heating in a reactor prior to use in the process of this invention, or are converted to another form under the described reaction conditions, but such materials still function as an effective catalyst in the defined process to give acetylene removal or destruction. For example, the metal may be present as the nitrates, carbonates, hydroxides, acetates, sulfites, silicates, sulfides and the like. For instance, iron nitrate and iron sulfate may be converted at least to some extent to the corresponding oxides while being heated in a reactor to a reaction temperature of about 550° C. Such salts of the defined metal groups, which are normally stable at the defined reaction temperatures may likewise be effective under the conditions of the described reaction. However, some metal compounds are more effective than other compounds of the same metal and, therefore, the compound giving the most effective results can be chosen. Preferably, catalysts, which are solid under the conditions of acetylene removal, will be used. Preferably, the compound will exhibit some basicity, e.g., as in the case of oxides, carbonates, or hydroxides.

Examples of a preferred catalyst would comprise, in addition to Fe and Ni, at least one metal selected from the group consisting of Cr, Mn, Cu, Zn and Zr, at least one alkali metal selected from the group consisting of Li, Na, K and Rb and at least one alkaline earth metal selected from the group consisting of Mg, Ca, Sr and Ba.

In the Periodic Table Group 8 elements in addition to Fe and Ni, the platinum group metals are preferred. Useful compounds include, for example, beryllium oxide, magnesium acetate, magnesium bromide, magnesium oxide, magnesium iodide, calcium oxide, calcium acetate, calcium oxalate, calcium chloride, calcium bromide, calcium iodide, calcium fluoride, calcium carbonate, strontium nitrate, stronitium chloride, strontium oxide, strontium hydroxide, strontium carbonate, strontium bromide, barium oxide, barium chloride, barium hydroxide, barium sulfate, barium bromide, barium iodide, beryllium chloride, cupric bromide, cuprous chloride, cuprous oxide, cupric oxide, cuprous silicide, cuprous sulfide, cupric phosphate, silver oxide, zinc fluoride, zinc oxide, zinc ortho phosphate, zinc phosphide, zinc orthosilicate, zinc metasilicate, zinc sulfide, cadmium oxide, titanium dioxide, zirconium oxide, $CrBr_2$, $Cr_2O_3$, magnesium dioxide, manganese disilicide, ferrous oxide, ferric oxide, $Fe_3O_4$, and the like and mixtures thereof. The term "mixtures thereof" includes compounds thereof, such as the ferrites. For example, a catalyst would include zinc ferrite in combination with barium oxide and $Na_2CO_3$.

The platinum metal elements are the elements in the Fifth and Sixth Periods of Group 8 of the Periodic Table. These elements are ruthenium, rhodium, palladium, osmium, iridium, and platinum. Preferred catalysts are platinum, palladium, compounds thereof, and mixtures of these. Suitable catalysts are such as palladium metal, palladium monooxide, platinum oxide(ous), platinum metal, platinum-rhodium alloys and the like. The elements of Groups 1a, 1b, 2a, 2b, 4b, 6b, 7b and 8 as defined are the main active constitutents of the catalyst. Alkali metals may be preferably present in an amount up to 40 weight percent of the other metallic elements (calculated as the elements) but normally will range from about 0.5 to 30 weight percent. The preferred alkali metals are potassium, sodium, rubidium, lithium and mixtures. Aluminum can be present in fairly large amounts but the exact function of aluminum is not known as aluminum by itself does not particularly catalyze the reaction. Non-metals such as silica can be present. Oxides, hydroxides, or carbonates or compounds, which are converted to these compounds under the conditions of reaction to destroy the carbonyl compounds, are preferred. Ingredients or anions which suppress or deactivate the effect of the defined metal elements should be avoided.

A preferred type of catalyst is one which comprises iron and especially preferred are those that comprise iron as the major metal or cation component by weight. Another preferred catalyst is Fe, Ni and Zn. The iron and other compounds can be present as oxides or other compounds or may be present as e.g. hydroxides, carbonates, nitrates, acetates, etc. One form is as ferrites, such as magnesium ferrite, manganese ferrite, calcium ferrite, barium ferrite, strontium ferrite, zinc ferrite, magnesium chromium ferrite, zinc chromium ferrite, calcium zinc ferrite, zinc nickel ferrite, mixtures thereof and the like. The ferrites may contain more than one metal as illustrated. Methods of preparing ferrites are disclosed, e.g., in U.S. Pat. No. 3,284,536; U.S. Pat. No. 3,270,080; U.S. Pat. No. 3,303,235; U.S. Pat. No. 3,334,152; U.S. Pat. No. 3,342,890; U.S. Pat. No. 3,526,675 and so forth. Mixtures of iron oxide with other compounds such as oxides have given excellent results. Thus, iron and nickel can be combined as a compound or other combination such as a ferrite or as a mixture of compounds with at least one metal from the group of alkali metals such as Li, Na, K, Rb, alkaline earth metals such as Mg, Ca, Sr, Ba, Group 4b metals such as Ti, Group 6b metals such as Cr, Group 7b metals such as Mn, Group 8 metals such as Co, Group 1b metals such as Cu, Group 2b metals such as Zn. Additionally, e.g., Al, Si, P, Bi may be present. Examples of mixtures of iron oxide with other compounds may be found in U.S. Pat. No. 2,461,147 and U.S. Pat. No. 3,308,193.

The Ni present in the present catalyst may be present in a combined form such as in a Zn Ni ferrite or as a separate compound such as Zn ferrite and NiO. The amount of nickel employed is minor and, although not critical, usually from 0.25 to 20 weight percent of nickel based on total catalyst weight (excluding support) will be present, or more preferably 1 to 10 weight percent.

Another aspect of the present invention in regard to purifying the effluent from oxidative dehydrogenations is the presence of carbonyl* compounds as impurities. These materials are also present in small, difficulty removed quantities and are quite detrimental to the ethylenically unsaturated hydrocarbon product. In a related application, Ser. No. 223,363 filed Feb. 3, 1972, commonly assigned herewith, a process and catalyst are disclosed for removing the carbonyl compounds. A large number of operable catalysts are disclosed therein for removing carbonyl compounds; however, nickel in the form of 33 weight percent nickel ferrite on 67 percent alumina was found to be inoperable in that the catalyst coked and would not function. Other iron compounds not containing nickel were found to be highly satisfactory for removing carbonyl compounds. Thus, it was quite surprising and unexpected when the present catalyst employing nickel as an essential component was found to substantially reduce the acetylenic compounds and carbonyl compounds without coking. The particular effectiveness of the present compound may be attributed to the synergistic effect of all of the herein recited components notwithstanding the detrimental effect of nickel when employed with less than all of said essential components.

*Generally the carbonyl compounds will have 1 to 8 carbon atoms, e.g. from 1 to 6 carbon atoms when a $C_4$ to $C_6$ compound is being dehydrogenated, and will have from 1 to 2 carbonyl groups. Formaldehyde is included in this definition.

The present acetylenes reduction catalyst is also an excellent carbonyl reduction catalyst, hence, both functions are carried out by this catalyst with minimum loss of other hydrocarbons in the stream. Elimination of the Ni component from the present catalyst leaves a decarbonylation catalyst such as that described in the described application. Thus, the present invention may be viewed as an improvement in that prior decarbonylation catalyst wherein the improvement is the inclusion of an essential Ni component for the reduction of acetylenic compounds.

The following is offered as a proposed mechanism derived from the observation of the process and is not submitted as a limitation: It is believed that the metal and alkaline earth metal are the principal decarbonylation participants, the metal is a "catalyst" for the water gas reaction wherein hydrogen is among the products and the alkali metal is a promoter for the metal water gas "catalyst". The Ni is considered a hydrogenation catalyst whereby the acetylenic compounds are hydrogenated. The small amounts of hydrogen inherently present in the system appear sufficient to achieve this. In addition, these components can perform other functions and may have synergistic ramifications not presently known.

This system is not considered a likely oxidative dehydrogenation catalyst because of the presence of the alkali metal which has been observed to kill the effectiveness of some oxidative dehydrogenation catalysts. For example, the water gas reaction is relevant to keeping the catalyst clean by removing the coke that forms during the contacting. The water gas reaction is less important when there is oxygen present, however. In a typical use of the present invention, for example, where the present catalyst bed is immediately below or following an oxidative dehydrogenation, the reactant stream would be oxygen poor. Although oxygen could be injected, it probably would be best not to do so as explained hereinbelow.

Although the alkali metals are considered to be the principal promoter for the water gas "catalyst", the alkaline earth metals also have some capacity in this regard and can replace some of the alkali metal. This is particularly suitable where sufficient oxygen is present to aid in decoking the catalyst.

The present catalyst is preferably reduced prior to use. The reduction is carried out in any manner previously known, however, a flow of hydrogen through the catalyst for from 5 minutes to several hours, e.g. 5 hours at temperatures of 500° to 1600° F. is suitable. As little as 5 to 30 minutes time at 800°–1300° F. has been useful and similar results have been obtained at 3 hours in the same temperature range. Generally, the temperature will be around 900°–1100° F. The reduction has been observed to be beneficial to the acetylenes reduction. Other reducing compounds such as n-butane can be used to reduce the catalyst.

The catalysts of this invention may be used as such or may be coated on catalyst carriers. Catalyst carriers are known in the art and include such compounds as alumina, silica, silicon carbide and so forth. Diluents may also be incorporated into the catalyst so long as the diluent does not prevent the catalyst from functioning. Preferably the carrier should be low surface and low acidity.

The gaseous mixture to be treated containing the acetylenic compounds as an impurity may be obtained from a variety of sources. However, the invention is particularly suitable for the purification of gaseous effluents resulting from the oxidative dehydrogenation of organic compounds including hydrocarbons utilizing air or oxygen diluted with non-condensable diluents such as nitrogen or helium. Examples of oxidative dehydrogenation processes are disclosed, e.g. in U.S. Pat. No. 3,207,805; U.S. Pat. No. 3,284,536; U.S. Pat. No. 3,320,329; U.S. Pat. No. 3,342,890; and U.S. Pat. No. 3,476,824.

Organic compounds to be dehydrogenated may be acyclic, cycloaliphatic or alkyl aryl compounds of 3 or 4 to 9 carbon atoms, which contain at least two adjacent carbon atoms, each of which carbon atoms has at least one hydrogen atom attached. Olefins, diolefins or unsaturated compounds may be produced from more saturated compounds, e.g. butadiene-1,3 may be produced, from n-butane. A mixture of monoolefins and diolefins may also be produced such as a mixture of butadiene-1,3 and butenes from a feedstock of a mixture of n-butane and butene. Cyclohexane may be dehydrogenated to cyclohexene and/or benzene. Ethyl benzene or ethyl cyclohexane may be dehydrogenated to styrene. Good results may be obtained with an organic feed containing at least 50, such as at least 75, mol percent of an acyclic aliphatic hydrocarbon. Hydrocarbons of 4 to 5 carbon atoms having a straight chain of at least four carbon atoms, e.g., those having a single double bond have been used. Preferred are the monoethylenically unsaturated compounds or mixtures of saturated and monoethylenically unsaturated compounds. Hydrocarbons having from 4 to 8 carbon atoms constitute a preferred feed with n-butane, n-butene, isopentane, isopentene, ethyl benzene and mixtures thereof having given excellent results.

Oxygen will generally be supplied to the dehydrogenation zone in the range of about 0.20 mol of oxygen to 2.0 or 3.0 mols of oxygen per mol of hydrocarbon to be dehydrogenated. A preferred range for the oxygen is from about 0.3 to 1.50 mols of oxygen per mol of hydrocarbon to be dehydrogenated. Either air, oxygen or oxygen diluted with a diluent such as nitrogen, helium, and the like, may be utilized. The oxygen may be supplied in gaseous form or via a solid oxygen carrier such as in U.S. Pat. No. 3,420,911. Steam may be fed to the dehydrogenation zone in amounts such as from about 2 to 40 mols of steam per mol of hydrocarbon to be dehydrogenated. An advantageous range is from 2 to 20 mols of steam per mol of hydrocarbon.

The dehydrogenation reaction may be conducted in the absence of contact catalysts, but better results are obtained if the reaction is conducted in the presence of metal or metal compound catalysts. The dehydrogenation reaction may be a fixed or fluid bed reactor. Reactors conventionally used for the dehydrogenation of hydrocarbons to butadiene may be employed. The total pressure in the dehydrogenation zone may suitably be about atmospheric pressure. However, higher pressures or vacuum may be used. Pressures such as from about atmospheric (or below) up to about 100 to 300 p.s.i.g. may be employed. The dehydrogenation reaction will normally be conducted at a temperature at least about 250° C. such as greater than about 300° C. or 375° C. and the maximum temperature in the reactor may be about 700° C. or 800° C. or perhaps higher such as 900° C.

The effluent from the dehydrogenation zone will contain the impure unsaturated organic products, various impurities including oxygenated hydrocarbons, noncondensable* gases and perhaps some unconverted feed, oxygen and steam. If air is used as the source of oxygen, nitrogen will be present in relatively large quantities as a noncondensable gas. Steam may be present in an amount up to 96 mol percent of the total effluent, such as from about 5 to 96 percent. On a water free basis the organic phase including dehydrogenated product, any unreacted feed, oxygenated hydrocarbons, polymer and tar and precursors thereof and any organic decomposition products usually range from about 1 to 50 mol percent of the effluent and generally will be within the range of or about 3 to 30 mol percent of the effluent. Also on a water free basis the noncondensable gases, such as nitrogen or $CO_2$, will usually be present in an amount of from or about 5 to 93 mol percent of the total effluent, but more often will be within the range of about 20 or 40 to 80 mol percent.

*The term "noncondensable" or "inert noncondensable" gases refers to those gases, other than hydrocarbons, such as nitrogen, $CO_2$ and CO, which do not condense under the conditions encountered.

In those uses wherein the effluent stream passing over the present catalyst is deficient in oxygen, particularly less than 1 mole percent of the reactor effluent, the water gas reaction becomes an important consideration and some steam becomes essential to the successful operation of the catalyst in a commercial manner. If the effluent stream is derived from an oxidative dehydrogenation, steam will normally be a usual constituent of the effluent stream and in substantial quantities, i.e., 3 to 30 mols of steam per mole of total organic compound (for example, unsaturated hydrocarbon and carbonyls).

The effluent gases leaving the dehydrogenation zone will generally be at a temperature of at least 400° C. or 450° C. with suitable ranges being between 450° C. or 500° C. and 800° or 900° C. depending upon the particular dehydrogenation process. According to the preferred embodiment of this invention the gases are fed directly into the catalyst bed for the removal of acetylenic compounds or at least are fed to the catalyst bed prior to condensation of steam from the effluent gases. This catalyst bed may be incorporated into the same reactor chamber as the dehydrogenation bed. Inert packing material may optionally be added between the dehydrogenation catalyst and the carbonyl destruction catalyst. Generally, the reactor effluent will not cool appreciably before the acetylenes removal catalyst is encountered and, therefore, the temperature will be within the same ranges as for the reactor effluent. Optionally, prior to contacting with the acetylenes removal catalyst the gaseous feed may be cooled or heated to give an optimum temperature for carbonyl destruction without adversely affecting the product. Also, it is within the scope of the invention to remove portions or components of the reactor effluent prior to contacting with the catalyst. Normally, the composition fed to the acetylenes removal catalyst will contain at least 3 or 5 mols of uncondensed steam per mol of total organic compound such as hydrocarbon and may contain e.g., from 3 to 30 mols of steam. The reactor effluent will generally contain less than 5 mol percent free oxygen and may initially contain less than one mol percent of the reactor effluent. It is possible to add oxygen to the reactor effluent prior to contacting with the acetylenes removal catalyst.

The presence of oxygen can be very detrimental in that the present acetylenes removal catalysts tend to completely oxidize the unsaturated compound, e.g., hydrocarbon products. Hence, although oxygen can help keep the catalyst from coking, it may do so as the sacrifice of unsaturated product. For this reason, the present invention is carried out with less than 5 mol percent and preferably less than 1 mole percent free oxygen present in the feed passing over the present catalyst (on a steam free basis).

As noted above, the nature of the feed streams to acetylenic compound reduction catalyst is usually such that a small amount of free hydrogen based on organic components may be present, usually 10 mol percent or less, and more preferably 1 mol percent or less. There may be from or about 0.5 mol percent of hydrogen present or more preferably 1 mol percent. The presence of hydrogen may be essential if the mechanism of acetylenic compound reduction involves hydrogenation. However, the mechanism may not involve hydrogen at all or if it does, the mechanism may be other than hydrogenation. In any event, hydrogen has been observed in the feed stream leaving the acetylenic compound reduction catalyst.

Hydrogen may be added to the feed streams to bring the content of the stream within ranges set out above. The absence of hydrogen or a lesser amount than described above may not effect the present invention. Since only minute quantities of acetylenes are usually being handled, sufficient hydrogen may be generated in situ for utilization, if as noted hydrogen is utilized.

The gaseous composition to be fed to the acetylenes removal catalyst zone will preferably comprise, exclusive of any water present, about or from 3.5 to 80 mol percent of unsaturated hydrocarbon, about or from 0.0005 to 2.5 mol percent of carbonyl compounds, about of from 0.0001 to 2.5 mol percent acetylenes and about or from 5 to 93 mol percent of noncondensable gases (i.e. noncondensable under the conditions of contact with the catalyst) all based on the total mols of gaseous composition being fed to the catalyst.

After the catalyst has been used for a period of time it may be regenerated such as by oxidation with air and/or with steam. Procedures for the regeneration of dehydrogenation catalysts to remove coke may be employed.

The following examples are only illustrative and are not intended to limit the invention. All percentages are by weight unless expressed otherwise.

In each of the examples, the same catalyst composition was employed for the oxidative dehydrogenation, i.e., a zinc ferrite.

EXAMPLES 1 TO 8

Bench scale runs were made on several catalyst compositions for the removal of acetylenes. The reactor was a 24 inch long, 1 inch I.D. stainless steel tube inserted in a 3100 watt furnace having three separate temperature control elements. The upper 8 inches serves as a steam super heater. The hydrocarbon feed was injected into the super heated steam prior to the steam entering an oxidative dehydrogenation catalyst bed of about 10 inches length. Below the oxidative dehydrogenation catalysts and separated therefrom by a thin bed of inert grain a 5 inch acetylene removal bed is located. The effluent is sampled above the acetylene removal bed and below. Analyses were by gas-liquid chromatographic methods.

The feed to the oxidative dehydrogenation catalyst (same for each example) was 99 percent butene-2, the balance being butadiene and n-butane, the feed contained no acetylenes or carbonyl compounds, LHSV 1.50 over the oxidative dehydrogenation zone, 0.55 mol oxygen (fed as air) per mol of hydrocarbon and 20 mols of steam per mol of hydrocarbon. The inlet temperature to the oxidative dehydrogenation zone was 660° F. and the temperature in the acetylene removal catalyst zone was about 1000° to 1050° F. Each run was carried out for varying periods with the results given here being taken after several weeks on stream.

EXAMPLE 1

An acetylene removal catalyst was prepared as follows: 6805 grams of $ZnFe_2O_4$, 1135 grams $BaCO_3$ (FMC), and 890 gms of $NiCO_3$ (49.4 percent Ni-Bakers Reagent) were dry mixed together. 1246 grams of NaOH (Bakers Reagent) were put into solution with 2.83 liters of distilled $H_2O$. This solution was added to the dry mix and made into 3/32 inch diameter pellets which were dried. The acetylene catalyst was tested as described above. The oxidative dehydrogenation catalyst gave a conversion/selectivity and yield for butadiene of 74, 95, and 70 mol percent respectively. The following by-products* were analyzed prior to and after passing the stream over the acetylene removal catalyst:

|  | Above Bed | Below Bed |
| --- | --- | --- |
| Formaldehyde | 2000 ppm | 40 ppm |
| Acetaldehyde | 1000 ppm | 200 ppm |
| Acrolein | 200 ppm | 40 ppm |
| Vinylacetylene | 1800 ppm | 180 ppm |

In each of the following examples similar catalyst preparative methods were employed. The results are reported in terms of the precent reduction of the by-product component in the stream.
*The by-products are based on butadiene.

EXAMPLE 2

| Catalyst composition 6:1$ZnFe_2O_4$:$BaCO_3$ + 7.5 percent Na | |
| --- | --- |
|  | % Reduction |
| Formaldehyde | 98 |
| Acetaldehyde | 75 |
| Acrolein | 80 |
| Vinylacetylene | 13 |

EXAMPLE 3

| Catalyst Composition: 6:1$ZnFe_2O_4$:$BaCO_3$ 7.5% Na 1.0% Ni | |
| --- | --- |
|  | % Reduction |
| Formaldehyde | 100 |
| Acetaldehyde | 80 |
| Acrolein | 80 |
| Vinylacetylene | 65 |

EXAMPLE 4

| Catalyst composition 6:1$ZnFe_2O_4$:$BaCO_3$ + 7.5 percent Na + 3 percent Ni | |
| --- | --- |
|  | % Reduction |
| Formaldehyde | 98 |
| Acetaldehyde | 80 |
| Acrolein | 80 |
| Vinylacetylene | 80 |

EXAMPLE 5

| Catalyst composition 6:1$ZnFe_2O_4$:$BaCO_3$ + 7.5 percent Na + 10 percent Ni | |
| --- | --- |
|  | % Reduction |
| Formaldehyde | 98 |
| Acetaldehyde | 80 |
| Acrolein | 85 |
| Vinylacetylene | 95 |

EXAMPLE 6

| Catalyst composition 6:1$ZnFe_2O_4$:$BaCO_3$ + 7.5 percent Na + 0.10 percent Pt | |
| --- | --- |
|  | % Reduction |
| Formaldehyde | 95 |
| Acetaldehyde | 40 |
| Acrolein | 40 |
| Vinylacetylene | 5 |

EXAMPLE 7

| Catalyst composition 6:1$ZnFe_2O_4$:$BaCO_3$ + 7.5 percent Na + 5.0 percent Cu | |
| --- | --- |
|  | % Reduction |
| Formaldehyde | 95 |
| Acetaldehyde | 40 |
| Acrolein | 40 |
| Vinylacetylene | 9 |

EXAMPLE 8

| Catalyst composition 6:1$Fe_2O_3$:$BaCO_3$ + 5.0 percent Na | |
| --- | --- |
|  | % Reduction |
| Formaldehyde | 95 |
| Acetaldehyde | 75 |
| Acrolein | 75 |
| Vinylacetylene | 10 |

EXAMPLES 9 AND 10

For further verification of these results, catalyst compositions, according to Examples 2 and 4 were tested under the same conditions in a large scale pilot plant facility. Both showed excellent carbonyl removal however, there was very little improvement in acetylene removal with the non-invention composition (Example 8).

|  | Example 9. (Catalyst according to Ex. 2) *6:1ZnFe₂O₄:-BaCO₃ + 7.5% Na % reduction 83 days on stream | Example 10. (Catalyst according to Ex. 4) *6:1ZnFe₂O₄:BaCO₃ + 7.5% Na + 3.0% Ni % reduction days on stream | |
| --- | --- | --- | --- |
|  |  | 35 | 71 |
| Formaldehyde | 98 | 100 | 98 |
| Acetaldehyde | 75 | 80 | 76 |
| Acrolein | 80 | 90 | 78 |
| Vinylacetylene | 15 | 80 | 90 |

*Reduced with $H_2$ before being brought on stream.

EXAMPLES 11 AND 12

A run was made through 25 cc of catalyst of 6 to 8 mesh (U.S. Standard in a one inch Vycor reactor controlled in a range of 559° to 575° C. The feed to the reactor contained

|  | ml/min |
| --- | --- |
| aldehyde solution (50/50 mixture of HCHO and CH₃CHO) | 6 |
| nitrogen | 720 |
| butadiene-1,3 | 575 |
| CO₂ | 210 |

The results were taken at the end of 80 minutes. The catalyst was 33 weight percent nickel ferrite deposited on 67 weight percent alumina carrier. The catalyst coked rapidly. A 33 weight percent strontium ferrite deposited on 67 weight percent alumina carrier did not coke and gave 79 percent carbonyl removal under the same conditions.

EXAMPLE 13

A catalyst for removing acetylenic and/or carbonyl compounds from a gaseous product stream is commercially valuable only if the materials which are considered products are not also removed in the process, or if they are removed that only small portions thereof are lost. The present example employs a catalyst such as used in Example 4, i.e., 6: 1 ZnFe₂O₄:BaCO₃+7.5% Na+3% Ni. The catalyst was run in a pilot plant facility and the change in the product material balance of feed stream entering and leaving the reduction catalyst was given particular attention.

The reactor employed contained an oxidative dehydrogenation catalyst followed by the acetylenes reduction catalyst. The two beds were separated by a substantially inert bed of AMC. The LHSV (Liquid Hourly Space Velocity) of the stream had been varied over the duration of the run to make certain observations but had been between 2.0 and 3.0 at all times. The steam to hydrocarbon mol ratio for the run as 12.0. The steam to oxygen ratio for the run was 24±0.7 and the oxygen to n-butene mol ratio was 0.52 for the run. The LHSV for the run is given in table.

| LHSV | Sequential Hours of Run |
| --- | --- |
| 2.49 | 1–335 |
| 2.00 | 335–401 |
| 2.49 | 401–446 |
| 3.00 | 446–572 |
| 2.00 | 572–671 |
| 2.49 | 671–812 |
| 3.00 | 812–921 |
| 2.00 | 921–992 |
| 2.49 | 992–1141 |
| 2.00 | 1141–1448 |

The feed to the acetylene catalyst comprised butadiene, n-butenes, CO₂, CO and trace amounts of acetylenes and carbonyls. The focus of this run was to determine the detriment, if any, of the catalyst on the butadiene product and unreacted n-butenes. The average was probably more meaningful than the particular time report since, as in any actual process, the numerical data varied considerably with some readings indicating loss of butadienes and some indicating increases, for example. The average indicates a small hydrocarbon loss which would be expected. During these runs spot analysis of acetylene and carbonyl content indicated substantial reduction of both. The results provided on acetylenes and carbonyl removal were not necessarily determined from the same sample as the product material balances but were made within the same time frame and show the continuing effectiveness of the catalyst.

During the course of the 1448 hour run 89 separate determinations of the material balance of C₄ over the acetylenes reduction catalyst were made. There were wide variations noted in different sampling which can be accepted as actual variations or which can be considered the result of chromatographic analysis variation or combination thereof. The results reported here are the cumulative averages of the changes in content of the stream after it has passed over the acetylene reduction catalyst. The results are reported in C₄ equivalents per 100 mols of C₄ fed. The run was terminated because of a drop in acetylenes reduction. Upon examination of the acetylenes removal catalyst, it was found to be fused at the upper portion. There appeared to have been an upset wherein water was flooded onto the catalyst.

| Hours Included | No. of samples* in Avg. determination | Averages Change In Stream After Passage Over Catalyst $C_4$ Equivalents/100 Mols of $C_4$ Fed | | | |
| --- | --- | --- | --- | --- | --- |
| | | CO | $CO_2$ | $C_4$ | Butadiene |
| 0–513 | 37 | −.163 | .873 | −.209 | −.410 |
| 513–1448 | 52 | −.082 | .874 | .095 | −.829 |
| 0–1448 | 89 | −.116 | .874 | −.031 | −.656 |

*A measurement above and below the acetylenic compounds reduction catalyst is considered one sample.

It should be particularly noted that there is no indication of dehydrogenation since butadiene content shows a slight loss.

Chromatographic analysis showed reduction of impurities as:

| | Mol % removal | |
| --- | --- | --- |
| | 600 hours | 840 hours |
| Formaldehyde | 99 | 100 |
| Vinylacetylene | 90 | 86 |
| Acetaldehyde | 88 | 85 |
| Acrolein | 60 | 75 |

EXAMPLE 14

Concurrently with the pilot plant run, a bench scale run according to the procedure of Examples 1–8 was set up with the same catalyst. After 60 days on stream no time trend was noted. Impurity removal from a $C_4$ stream similar to that employed in Example 11 showed:

| | Mol % Reduction |
| --- | --- |
| Formaldehyde | 100 |
| Vinylacetylene | 90 |
| Acetaldehyde | 93 |
| Acrolein | 85 |

EXAMPLES 15 AND 16

These examples compare an acetylene removal catalyst according to the present invention, i.e., containing nickel and one employing cobalt in place of nickel. Substantially, the same procedure as employed as in Example 1 for the catalyst preparation. The components are:

| Example 15 | Example 16 |
| --- | --- |
| 784 grams $Fe_2O_3.XH_2O$ (87% iron) | 784 grams $Fe_2O_3.XH_2O$ (87% iron) |
| 213.3 grams $NiCO_3$ | 214.6 grams $CoCO_3$ |
| 250 grams NaOH | 250 grams NaOH |
| 113.4 grams $BaCO_3$ | 113.4 grams $BaCO_3$ |
| 340 grams $H_2O$ | 340 grams $H_2O$ |
| 3/32" dia. pellets | 3.32" dia. pellets |
| Composition Wt. % | Composition Wt. % |
| 59.6:9.85 Fe:Ba (6:1 ratio) | 59.6:9.85 Fe:Ba (6:1 ratio) |
| 8.11% Na | 8.11% Na |
| 12.45% Ni | 12.45% Co |

Hydrocarbon Feed

Butene-2 93.28%, the balance being butadiene (∼2.3%) and n-butene and containing no acetylenes or carbonyl compounds was fed to a zinc ferrite oxidation dehydrogenation catalyst under the following conditions:

2.0 LHSV
15/1 Steam/hydrocarbon
0.55/10 $O_2$/hydrocarbon
Inlet 620° F.; Outlet 1045° F.

The same reactor as employed in Example 1 was employed with the effluent passing from the oxidation dehydrogenation zone directly into the acetylene removal bed. The inert bed was omitted.

The results of acetylene removal over about 16 days are:

| | Ex. 15 % reduction (mole) | Ex. 16 % reduction (mole) |
| --- | --- | --- |
| Carbonyls | 100% | 100% |
| Vinylacetylene | 100% | 75% |

Thus, although Co as a component of the catalyst, does remove some acetylene, as compared to Ni it is not as valuable or desirable since there is a large proportion of acetylene left. The relative effect of the two catalyst beds on the desired butadiene produced can be compared by comparing the conversion, selectivity and yield from the reactor (after the two beds).

| Ex. 15 | Ex. 16 |
| --- | --- |
| mole % butadiene C/S/Y | mole % butadiene C/S/Y |
| 72/95/69 | 73/94/69.5 |

The cobalt results in a slightly reduced selectivity. Catalysts of the type disclosed in Example 15 have been run as long as a year with only slight decline in vinylacetylene removal.

The invention claimed is:

1. In a vapor phase process for the preparation of hydrocarbon monoolefins and diolefins comprising oxidative dehydrogenation of a stream of $C_3$ to $C_9$ hydrocarbon compounds to produce a product stream comprising, exclusive of any water present, 3.5 to 80 mol percent hydrocarbon monoolefins and diolefins and about from 0.0001 to 2.5 mol percent acetylenic compound impurity, about from 0.0005 to 2.5 mol percent carbonyl compounds and 5 to 93 mol percent non-condensable gases, wherein the improvement comprises contacting said product stream in vapor phase at a temperature in the range of 250° to 900° C. and containing less than 5 mol percent free oxygen with a solid catalyst for reducing said acetylene compounds in said product stream, said catalyst consisting essentially of zinc ferrite and nickel oxide, wherein Fe is the major metal component by weight, an alkaline earth metal oxide, carbonate or hydroxide of Mg, Ca, Sr or Ba, and about 0.5 to 30 weight percent of an alkali metal oxide, carbonate or hydroxide, based on the other metallic elements of Li, Na, K or Rb said Ni being present in the range of 0.25 to 20 weight percent of the total weight of the catalyst, and recovering said product stream having the amount of acetylenic compounds therein reduced.

2. The process according to claim 1 wherein Ba and Na are present and the major amount of hydrocarbons in said product stream are n-butene and butadiene.

3. The process according to claim 1 wherein the major amount of hydrocarbons in said hydrocarbon steam comprises n-butene and butadiene.

4. The process according to claim 1 wherein said hydrocarbons have 2 to 8 carbon atoms.

5. The process according to claim 4 wherein said hydrocarbons have 4 to 6 carbon atoms.

* * * * *